United States Patent
Seo et al.

(10) Patent No.: US 10,288,560 B1
(45) Date of Patent: May 14, 2019

(54) SYSTEM FOR OBSERVING CONFORMATIONAL CHANGE IN PROTEIN

(71) Applicant: KOREA INSTITUTE OF SCIENCE AND TECHNOLOGY, Seoul (KR)

(72) Inventors: Minah Seo, Seoul (KR); Young Min Jhon, Seoul (KR); Chulki Kim, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 0 days.

(21) Appl. No.: 15/997,947

(22) Filed: Jun. 5, 2018

(30) Foreign Application Priority Data

Mar. 13, 2018 (KR) ........................ 10-2018-0029305

(51) Int. Cl.
| | |
|---|---|
| *G01J 5/02* | (2006.01) |
| *G01N 21/3586* | (2014.01) |
| *G01N 33/68* | (2006.01) |
| *G02F 1/35* | (2006.01) |
| *G01J 3/42* | (2006.01) |

(52) U.S. Cl.
CPC ............ *G01N 21/3586* (2013.01); *G01J 3/42* (2013.01); *G01N 33/6845* (2013.01); *G01N 33/6896* (2013.01); *G02F 1/353* (2013.01); *G01N 2223/101* (2013.01); *G02F 2203/13* (2013.01)

(58) Field of Classification Search
CPC .............. G01J 5/0896; G01N 21/4738; G01N 2021/1742; G01N 2021/174; G01N 21/8422; G01N 21/552
See application file for complete search history.

(56) References Cited

U.S. PATENT DOCUMENTS

| | | | |
|---|---|---|---|
| 7,411,673 B2 * | 8/2008 | Gould ...................... | G01J 3/02 250/458.1 |
| 2008/0014580 A1 | 1/2008 | Alfano et al. | |
| 2008/0137068 A1 * | 6/2008 | Ouchi ................ | G01N 21/3581 356/51 |
| 2011/0070655 A1 * | 3/2011 | Horiuchi ............. | B01L 3/50273 436/174 |
| 2013/0136744 A1 * | 5/2013 | Bouche .................. | C07K 16/18 424/135.1 |
| 2016/0202178 A1 * | 7/2016 | Acosta ................... | G01N 21/27 356/303 |

FOREIGN PATENT DOCUMENTS

KR 10-2011-0027143 A 3/2011

* cited by examiner

*Primary Examiner* — David P Porta
*Assistant Examiner* — Mamadou Faye
(74) *Attorney, Agent, or Firm* — Rabin & Berdo, P.C.

(57) ABSTRACT

Disclosed is a system for observing the conformational change in a protein, which includes a sensing element which is configured to amplify an electromagnetic wave of a specific frequency; a light irradiation unit which is configured to irradiate a photoreceptor protein solution coated on the sensing element with light; an electromagnetic wave irradiation unit which allows an electromagnetic wave to be incident in a direction perpendicular to the bottom surface of the sensing element; a detection unit which is configured to detect an electromagnetic wave reflected from the bottom surface of the sensing element; and a control unit which is configured to observe the conformational change in the photoreceptor protein based on the detected electromagnetic wave.

8 Claims, 11 Drawing Sheets

SYSTEM FOR OBSERVING CONFORMATIONAL CHANGE IN PROTEIN

CROSS-REFERENCE TO RELATED APPLICATION

This application claims priority to and the benefit of Korean Patent Application No. 2018-0029305, filed on Mar. 13, 2018, the disclosure of which is incorporated herein by reference in its entirety.

BACKGROUND

1. Field of the Invention

The present invention relates to a system for observing the conformational change in a protein using an ultra-sensitive sensing element to observe the conformational change and dynamics of proteins (e.g., a small biomolecule and a neurotransmitter or neuromodulator) according to the activity change in various types of cells such as neurons in real time.

2. Discussion of Related Art

To understand the intercellular system of neuronal transmission, it is necessary to measure a small amount of existing neurotransmitters, and to trace the dynamics in which the conformational change occurs in a protein when a signal stimulus is given thereto. That is, there are demands for investigating the mechanism of intracellular or intercellular transmission of neural signaling, and to establish the theoretical basis of a bioscientific phenomenon and develop a method for treating a related nerve disease, for performing quantitative analysis such as space imaging for a trace amount of neurotransmitters and understanding a signaling system of neuronal transmission.

To measure the conformational change and dynamics of a protein receptor due to such an external stimulus (e.g., light, etc.), in addition to the external stimulus, it is essential to create an environment that can stably maintain activity without limiting the conformational change in a protein receptor. However, a buffer solution prepared based on water among factors constituting such an environment has very high absorbance in a terahertz region, and thus becomes a major factor that reduces a signal-to-noise ratio (SNR) of the system. Therefore, the buffer solution is a major obstacle to observing a signal change caused by the activity of a protein receptor.

For this reason, conventional methods for measuring the activity of a protein receptor require a large amount of solid-phase sample, or need to additionally use an ultra-low temperature apparatus to reduce SNR.

PRIOR ART DOCUMENTS

Patent Documents (Patent Document 1) Korean Unexamined Patent Application Publication No. 10-2011-0027143
(Patent Document 2) US Unexamined Patent Application Publication No. 2008/0014580

SUMMARY OF THE INVENTION

The present invention is directed to providing a system for observing the conformational change in a protein, which is used in contactless measurement of the conformational change occurring when a protein is activated through an optical (terahertz frequency or far-infrared region) measurement method using a sensing element.

The present invention is also directed to providing a system for observing the conformational change in a protein, which is used to sense the change in a small amount of signals when a trace amount of protein sample is activated using a sensing element and to measure the dynamics of signal transmission caused by the conformational change in protein molecules present in the cell membrane of various types of cells such as neurons in real time.

The present invention is also directed to providing a system for observing the conformational change in a protein, which is used to observe the conformational change and dynamics of receptors (e.g., G protein-coupled receptors (GPCRs) that activate G proteins, tyrosine kinase receptors, etc.) which are located in the cell membrane using an electromagnetic wave in the terahertz band (0.1 to 10.0 THz) in real time.

One aspect of the present invention, a system for observing the conformational change in a protein includes a sensing element which is configured to amplify an electromagnetic wave of a specific frequency; a light irradiation unit which is configured to irradiate a photoreceptor protein solution coated on the sensing element with light; an electromagnetic wave irradiation unit which allows an electromagnetic wave to be incident in a direction perpendicular to the bottom surface of the sensing element; a detection unit which is configured to detect an electromagnetic wave reflected from the bottom surface of the sensing element; and a control unit which is configured to observe the conformational change in the photoreceptor protein based on the detected electromagnetic wave.

Preferably, the sensing element includes a substrate; and a film disposed on the substrate, wherein the film may be subjected to intaglio patterning of rectangular slots so that an electromagnetic wave of a specific frequency is amplified.

Preferably, the slots may be adjusted in width, thickness and length so that resonance occurs at a frequency in the natural vibration mode of the photoreceptor protein.

Preferably, the light irradiation unit may include a light source which emits white light; a prism which separates the white light by wavelength; and a color filter which transmits only light with a specific wavelength out of light passing through the prism according to the wavelength dependence of the photoreceptor.

Preferably, the electromagnetic wave irradiation unit may allow an electromagnetic wave to be incident in a direction perpendicular to the bottom surface of the sensing element coated with a photoreceptor solution before the photoreceptor protein solution is irradiated with light by the light irradiation unit, the detection unit detects an electromagnetic wave reflected from the bottom surface of the sensing element, and the control unit measures a first reflectance based on the electromagnetic wave detected from the detection unit.

Preferably, the electromagnetic wave irradiation unit may allow an electromagnetic wave to be incident in a direction perpendicular to the bottom surface of the sensing element coated with the photoreceptor solution after the photoreceptor protein solution is irradiated with light by the light irradiation unit, the detection unit may detect an electromagnetic wave reflected from the bottom surface of the sensing element, and the control unit may measure a second reflectance based on the electromagnetic wave detected from the detection unit.

Preferably, the control unit may measure a rate of change in a photoreactive signal of the photoreceptor protein based on the first reflectance and second reflectance.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the advantages and characteristics of the present invention and the methods of accomplishing the same may be clearly understood by reference to the detailed description of exemplary embodiments and the accompanying drawings. However, the present invention is not limited to the exemplary embodiments disclosed below, and may be embodied in many different forms. These exemplary embodiments are merely provided to complete the disclosure of the present invention and fully convey the scope of the present invention to those of ordinary skill in the art, and the present invention should be defined by only the accompanying claims. Throughout the specification, like numerals denote like elements. The "and/or" includes all combinations of two or more and each of the mentioned items.

Although the "first, second, . . . " are used to describe various elements, components and/or sections, it is understood that these elements, components and/or sections are not limited by these terms. These terms are used only to distinguish one element, component or section from another element, component or section. Therefore, it is understood that the first element, component or section mentioned below may be the second element, component or section within the technical scope of the present invention.

The terms used herein are for describing embodiments and are not intended to limit the present invention. Herein, singular forms include plural forms unless specifically stated otherwise. The "comprises" and/or "comprising" used herein do not preclude the presence or addition of one or more other component, step and/or element, in addition to the mentioned component, step and/or element.

Unless defined otherwise, all terms (including technical and scientific terms) used herein may be used in a sense that is commonly understood by one of ordinary skill in the art to which the present invention belongs. Also, generally used predefined terms are not ideally or excessively interpreted unless explicitly defined otherwise.

Also, to explain the present invention, when detailed description on the related art is determined to unnecessarily obscure the subject matter of the present invention, the detailed description will be omitted. Moreover, the terms to be described below are defined in consideration of functions in an embodiment of the present invention, and may vary according to a user, the intention or custom of an operator. Therefore, the definition should be based on the contents spanning the entire specification.

Figure 1:
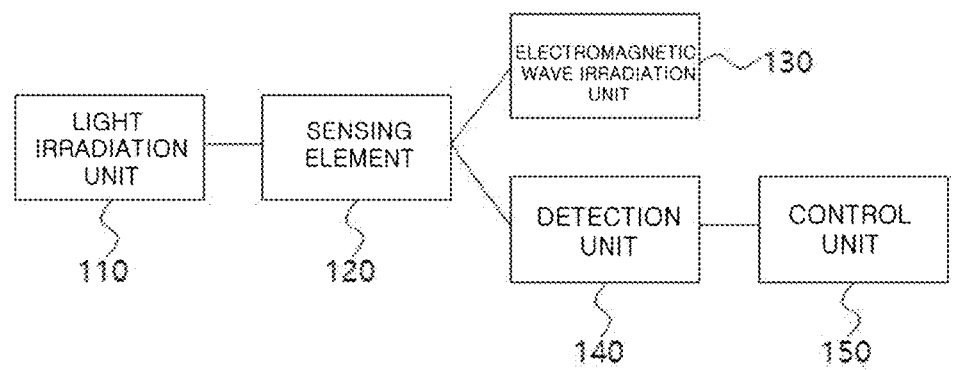
FIG. 1 is a block diagram of a system for observing the conformational change in a protein according to an exemplary embodiment of the present invention.

FIG. 1 is a block diagram of a system for observing the conformational change in a protein according to an exemplary embodiment of the present invention.

Referring to FIG. 1, a system for observing the conformational change in a protein 100 includes a light irradiation unit 110, a sensing element 120, an electromagnetic wave irradiation unit 130, a detection unit 140 and a control unit 150.

The light irradiation unit 110 irradiates a photoreceptor protein, which is an object used to observe a conformational change, with light to change the conformation of the photoreceptor protein.

Figure 2:
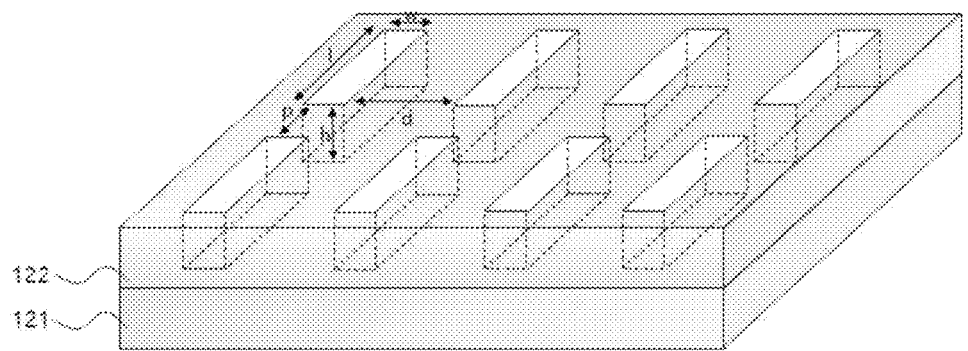
FIG. 2 is a diagram of a sensing element according to an exemplary embodiment.

The sensing element 120 is an element that amplifies an electromagnetic wave of a specific frequency, and the upper surface thereof is coated with a photoreceptor protein solution to observe a conformational change. In an embodiment, referring to FIG. 2, the sensing element 120 may include a substrate 121, and a film 122 disposed on the substrate 121, and the film 122 may be subjected to intaglio patterning of rectangular slots such that an electromagnetic wave of a specific frequency is amplified. Such conformation of the film 122 is called a metamaterial. Here, the substrate 121 of the sensing element 120 may consist of quartz, silicon, sapphire or glass, and the film 122 may consist of gold, silver, copper or aluminum. In addition, the slot of the film 122 of the sensing element 120 may be adjusted in width (w), length (l), height (h) and distances (d and p) between adjacent slots such that resonance occurs at a frequency in the natural vibration mode of a target protein in which the conformational change is observed. For example, the width (w) of the slot may be adjusted within 10 nm to 1 μm, the height (h) may be adjusted within 100 nm to 1 μm, and the length (l) may be adjusted within 10 μm to 1 mm.

The electromagnetic wave irradiation unit 130 may allow an electromagnetic wave to be incident in a direction perpendicular to the bottom surface of the sensing element 120 coated with the photoreceptor protein solution. Here, the electromagnetic wave may correspond to terahertz (THz).

The detection unit 140 detects the electromagnetic wave incident in the direction perpendicular to the bottom surface of the sensing element 120 by the electromagnetic wave irradiation unit 130, and then reflected from the bottom surface of the sensing element 120.

The control unit 150 observes the conformational change of the photoreceptor protein based on the electromagnetic wave detected by the detection unit 140. Preferably, when the detection unit 140 converts the signal of the electromagnetic wave reflected from the bottom surface of the sensing element 120 into an electrical signal, the control unit 150 may receive a corresponding electrical signal, thereby measuring the conformational change and dynamics of the photoreceptor protein from the electrical signal.

In an embodiment, the light irradiation unit 110, the sensing element 120, the electromagnetic wave irradiation unit 130, the detection unit 140, and the control unit 150 may be embodied as respective modules constituting the system for observing the conformational change in a protein 100, or as separate devices, and may be connected to each other with or without wires.

Figure 3:
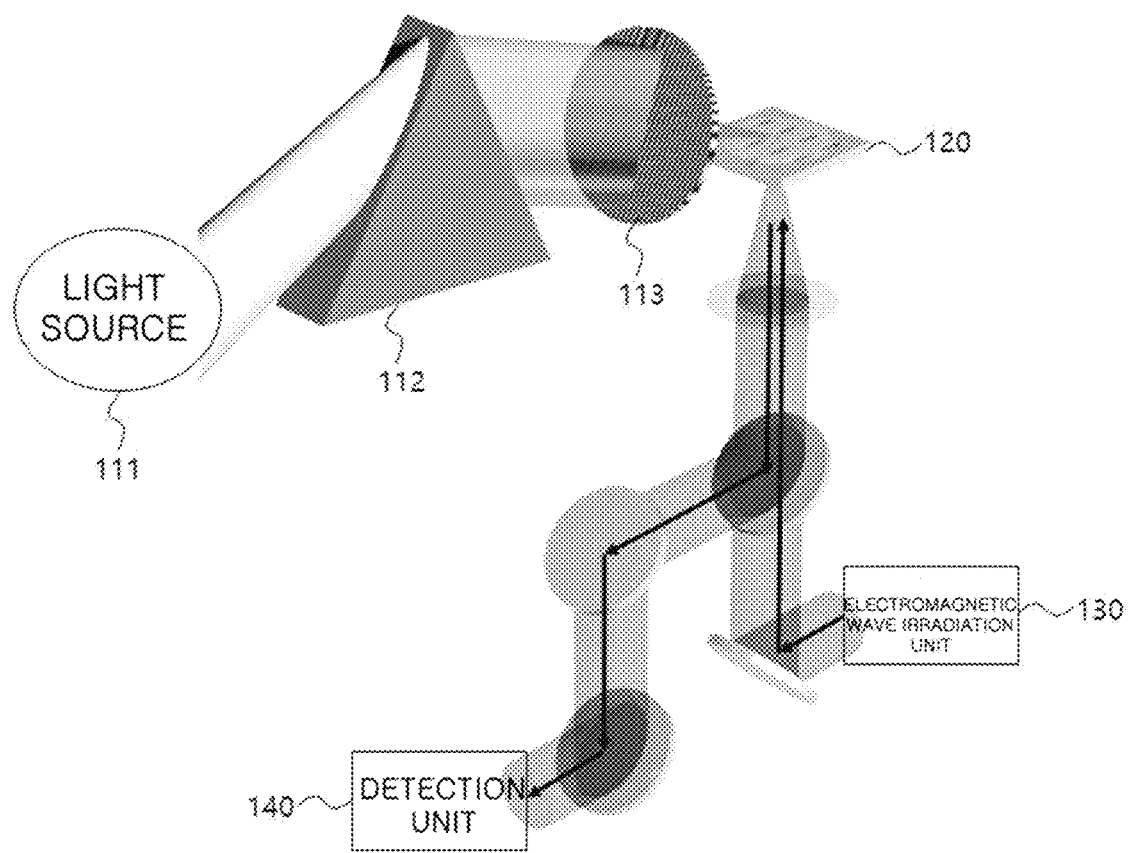
FIG. 3 is a diagram of a system for observing the conformational change in a protein according to an exemplary embodiment.
Figure 4:
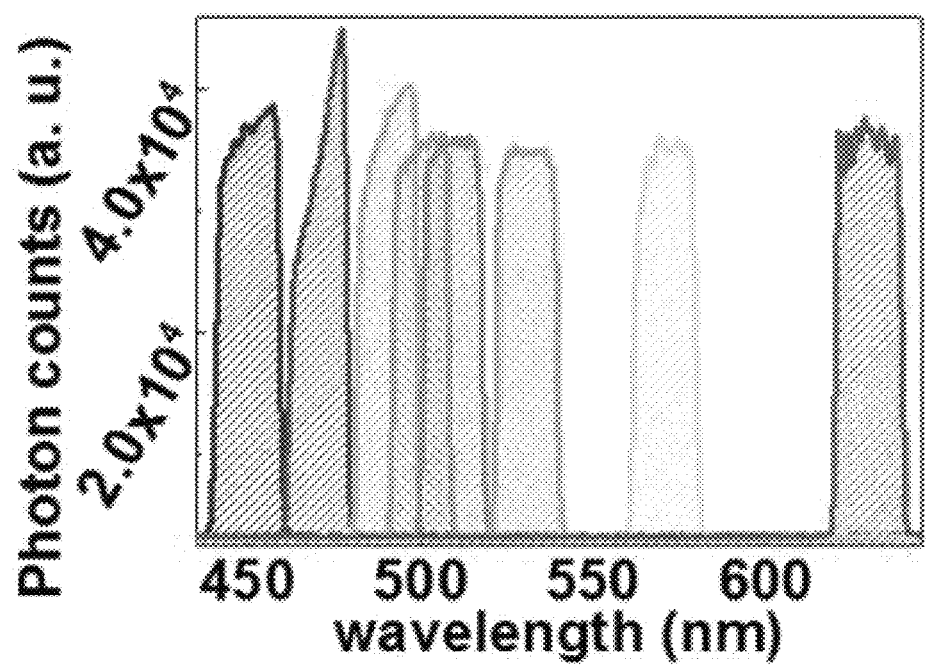
FIG. 4 is a graph showing incidence and reflection of electromagnetic waves with respect to a sensing element according to an exemplary embodiment.

FIG. 3 is a diagram of a system for observing the conformational change in a protein according to an exemplary embodiment.

Referring to FIG. 3, the system for observing the conformational change in a protein includes a light irradiation unit 110, which includes a light source 111, a prism 112 and a color filter 113, a sensing element 120, an electromagnetic wave irradiation unit 130, a detection unit 140 and a control unit 150, but the control unit 150 is not shown in FIG. 3.

Preferably, referring to FIG. 3, the system for observing the conformational change in a protein may include a half mirror-like component so that the electromagnetic wave emitted from the electromagnetic wave irradiation unit 130 is incident in a direction perpendicular to the sensing element 120, and the detection unit 140 is able to detect the electromagnetic wave reflected from the bottom surface of the sensing element 120, wherein the half-mirror like component merely corresponds to an embodiment that implements the system for observing the conformational change in a protein, and can be embodied by various methods. Hereinafter, referring to FIG. 3, a method of observing the conformational change in a protein in the system for observing the conformational change in a protein will be explained.

First, the top surface of the sensing element 120 is coated with a photoreceptor protein solution. Preferably, referring to FIG. 5, the photoreceptor protein solution may be applied to the part of the film 122 of the sensing element 120, in which a slot is formed.

The electromagnetic wave irradiation unit 130 allows an electromagnetic wave to be incident in a direction perpendicular to the sensing element 120 coated with the photoreceptor protein solution before the photoreceptor protein solution is irradiated with light by the light irradiation unit 110, and the detection unit 140 detects the electromagnetic wave reflected from the bottom surface of the sensing element 120. Preferably, referring to FIG. 5, when an electromagnetic wave is applied in a direction perpendicular to the sensing element 120, the electromagnetic wave is incident to the surface (shown in red) at which the photoreceptor protein solution is in contact with the sensing element 120, and the electromagnetic wave reflected from the corresponding surface is detected by the detection unit 140. The surface shown in red in FIG. 5 simultaneously corresponds to the surface with the largest field amplification of an electromagnetic wave (e.g., a terahertz electromagnetic wave) and the highest sensitivity to a photoreceptor protein.

The control unit measures a first reflectance based on the electromagnetic wave detected by the detection unit 140. Here, the first reflectance means an electromagnetic wave reflectance before the conformation of the photoreceptor protein is changed by light.

Then, the conformation of the photoreceptor protein applied to the sensing element 120 is changed.

Figure 5:
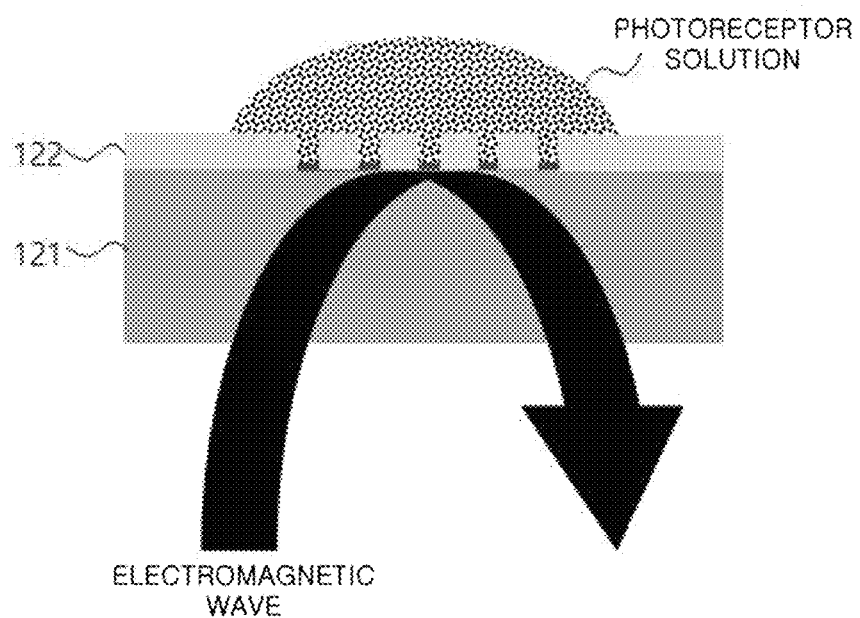
FIG. 5 is a diagram showing white light separated by wavelength.

More specifically, white light output from the light source 111 passes through the prism 112, and is separated by wavelength as shown in FIG. 5. Only light of a specific frequency of the light separated by wavelength passing through the color filter 113 is transmitted and applied to the photoreceptor protein. Here, the light with a specific wavelength transmitted through the color filter 113 may be predetermined according to the wavelength dependence of the photoreceptor protein, wherein the wavelength may correspond to a specific wavelength at which the photoreceptor protein is most sensitively reacted. For example, since rhodopsin (Rods) has the highest light absorption at a wavelength corresponding to 490 to 500 nm, in order to observe the conformational change in rhodopsin, only light of a wavelength corresponding to 490 to 500 nm can be allowed to be transmitted through the color filter 113. Light with a specific wavelength selected after being transmitted through the color filter 113 is applied to the photoreceptor protein solution to change the conformation of the photoreceptor protein.

The electromagnetic wave irradiation unit 130 allows an electromagnetic wave to be incident again in a direction perpendicular to the sensing element 120, the detection unit 140 detects the electromagnetic wave reflected from the bottom surface of the sensing element 120, and the control unit 150 measures a second reflectance based on the electromagnetic wave detected from the detection unit. Here, the second reflectance refers to an electromagnetic wave reflectance after the conformation of the photoreceptor protein has been changed by the light, and since the photoreceptor protein is changed in degree of absorption of an electromagnetic wave according to conformational change, in order to observe the conformational change of the protein in the present invention, the first reflectance measured before the conformational change in the photoreceptor protein and the second reflectance measured after the conformational change in the photoreceptor protein were used.

The control unit 150 may measure a rate of change in a photoreactive signal of the photoreceptor protein based on the first and second reflectances detected for the photoreceptor protein solution, thereby observing the conformational change in the photoreceptor protein. That is, in FIG. 5, the dynamics of the protein occurring on the surface at which the photoreceptor protein solution is in contact with the sensing element 120, shown in red, is observed.

Hereinafter, referring to FIGS. 6 to 10, a process of observing the conformational change in a protein will be described using a system for observing the conformational change in a protein such as rhodopsin.

Figure 6:
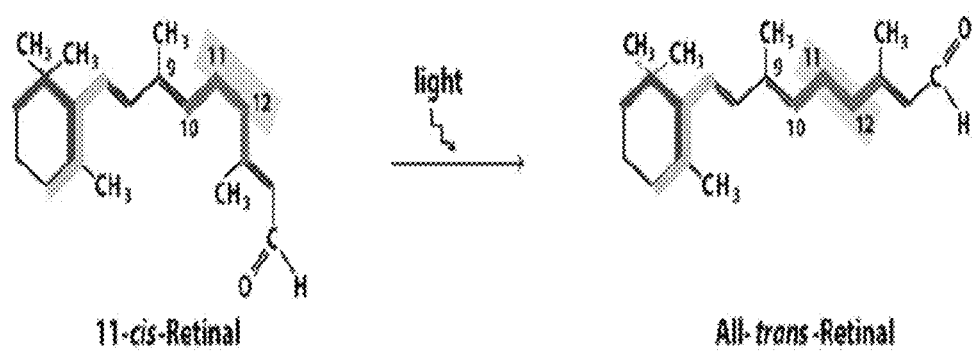
FIG. 6 is an exemplary diagram of a protein for explaining a process of observing the conformational change in a protein according to an exemplary embodiment.

Referring to FIG. 6, when 11-cis-retinal of rhodopsin is irradiated with light, a photoelectric reaction occurs, and rhodopsin is converted into the conformation of all-trans-retinal. Here, a process of constituting the system for observing the conformational change in a protein 110 will be explained focusing on the detection of all-trans-retinal.

The sensing element 120 is formed to have the following modes in a terahertz region among the natural vibration modes of the all-trans-retinal as resonance frequencies, and detects the photoreactivity of 11-cis-retinal. Here, the natural vibration mode means that each molecule is regularly folded and then stretched at a specific frequency, repeatedly.

0.8 THz: relative chain/ring bending ($C_6C_7C_8$; $C_{10}C_{11}C_{12}$)

1.0 THz: terminal chain torsion ($C_{10}C_{11}C_{12}C_{13}$; $C_{11}C_{12}C_{13}C_{14}$)

1.7 THz: ring torsion ($C_2C_1C_6C_5$; $C_4C_5C_6C_7$)+chain bending ($C_{10}C_{11}C_{12}$) Since the natural vibration modes of rhodopsin are exhibited at 0.8 THz, 1.0 THz and 1.7 THz, each of the sensing elements 120 having respective resonance frequencies was coated with a 11-cis retinal-attached receptor. The electromagnetic wave irradiation unit 130 applies electromagnetic waves corresponding to 0.8 THz, 1.0 THz and 1.7 THz, respectively, to corresponding sensing elements 120 coated with rhodopsin in a direction perpendicular to the sensing element 120, and the detection unit 140 detects an electromagnetic wave reflected from the bottom surface of the sensing element 120.

Figure 7A:
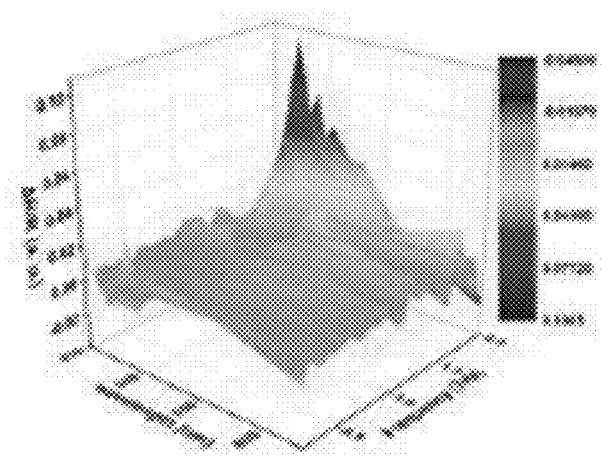
FIGS. 7a to 7c show graphs of the electromagnetic wave reflectance of a protein by wavelength.
Figure 7B:
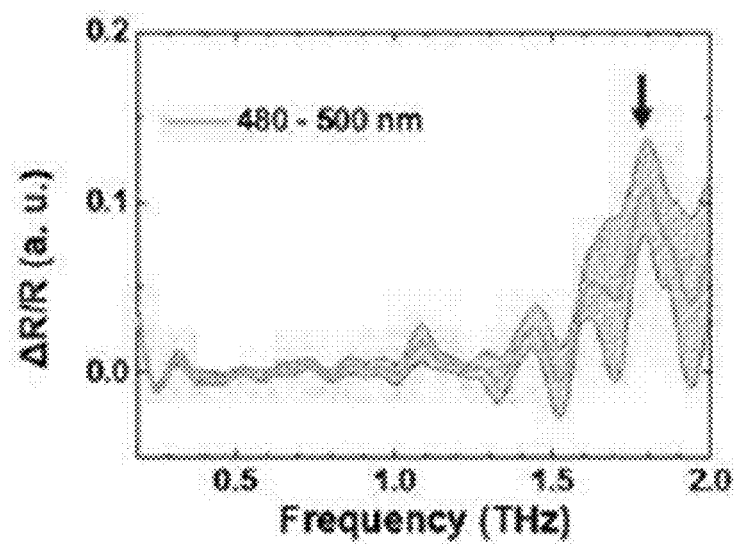
Figure 7C:
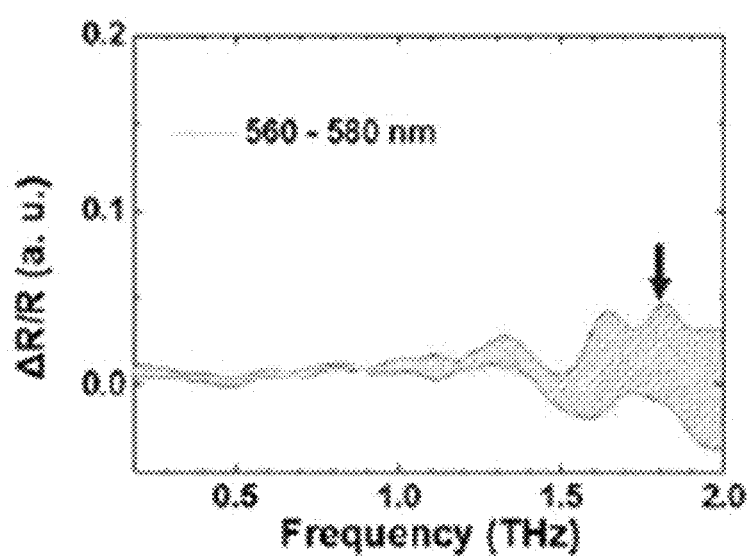

The light source 111 of the light irradiation unit 110 allows rhodopsin applied to the sensing elements 120 to be irradiated with a short-wavelength light source (e.g., 532-nm laser) with a wavelength of approximately 500 nm at which rhodopsin most sensitively reacts to an external light stimulus, resulting in a photoreaction. Referring to FIGS. 7a to 7c, the change in electromagnetic wave signals according to the wavelength with respect to rhodopsin is shown, and as shown in FIG. 7a, it can be seen that the terahertz light absorption (reflectance) of rhodopsin is changed according to wavelength. Referring to FIG. 7b, when light of 480 to 500 nm is irradiated, it can be seen that the terahertz light absorption (reflectance) of rhodopsin is high, representing that the conformational change in rhodopsin occurred. On the other hand, referring to FIG. 7c, when light of 560 to 580 nm is irradiated, it can be seen that the terahertz light absorption (reflectance) of rhodopsin is low, indicating that there was almost no conformational change in rhodopsin, and therefore it can be seen that the corresponding wavelength is a wavelength at which there is no photoreaction with respect to rhodopsin. In FIGS. 7b and 7c, the regions shown as a dotted line represent an error bar. That is, as described with reference to FIGS. 7a to 7c, since the conformational change in rhodopsin occurs at approximately 500 nm, rhodopsin is irradiated with a short-wavelength light source of approximately 500 nm by the light irradiation unit 110.

Figure 8A:
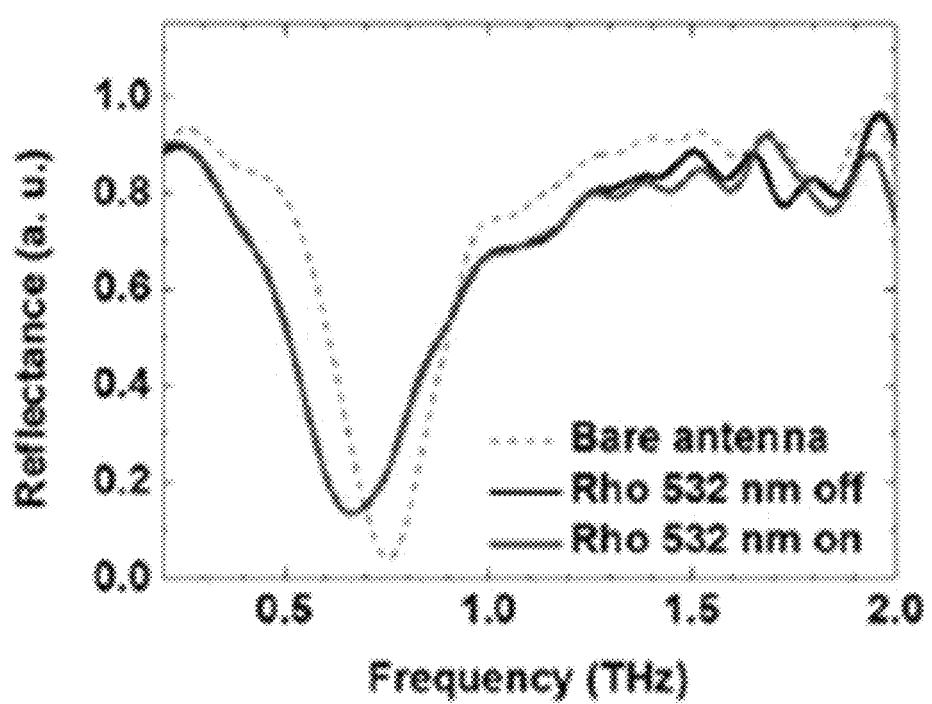
FIGS. 8a to 8c show graphs for illustrating a process of determining a frequency exhibiting the photoelectric reaction of a protein.
Figure 8B:
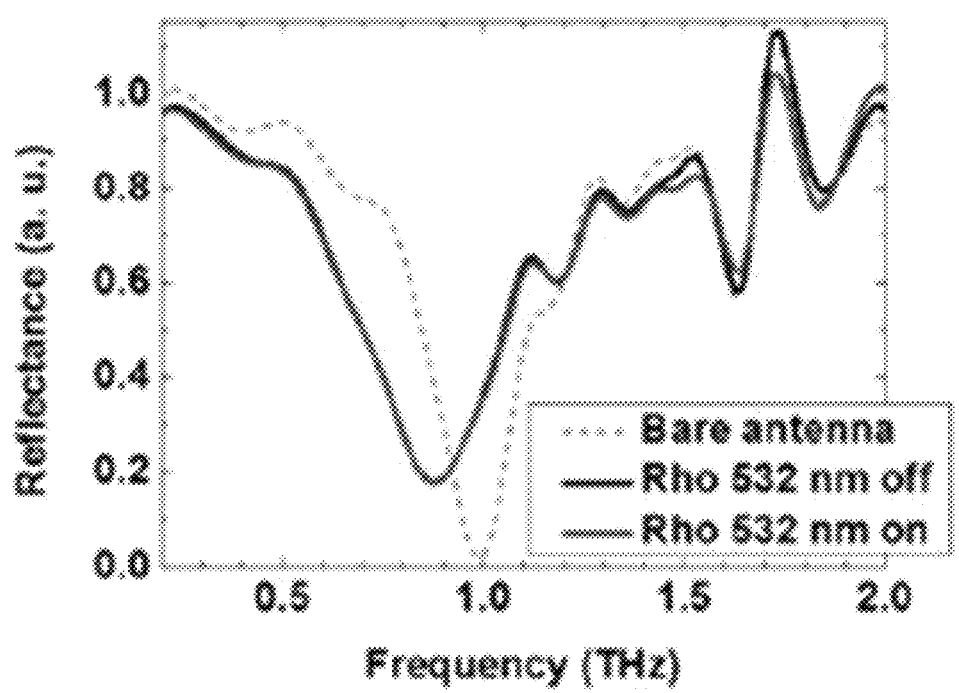
Figure 8C:
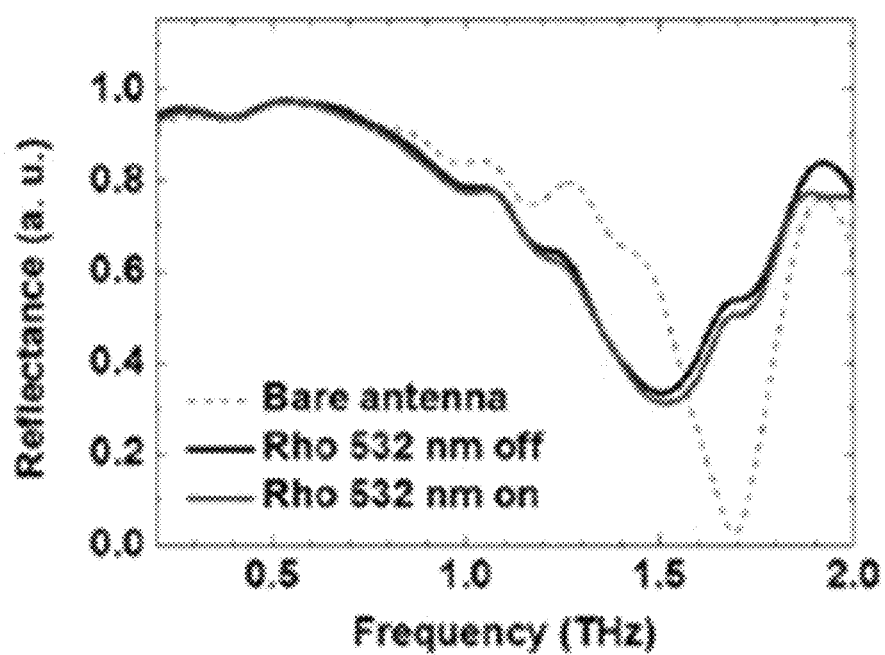

After the photoreaction occurs by irradiating rhodopsin with light, the electromagnetic wave irradiation unit 130 applies an electromagnetic wave in a direction perpendicular to the sensing element 120, and the detection unit 140 detects an electromagnetic wave reflected from the bottom surface of the sensing element 120. Signals of electromagnetic waves detected before and after the photoreaction of rhodopsin are as shown in FIGS. 8a to 8c. Referring to FIGS. 8a to 8c, each of 8a, 8b and 8c shows the result obtained by detection using the sensing element 120 having a resonance frequency of 0.8 THz, 1.0 THz or 1.7 THz, and bare antenna refers to a reflectance of the sensing element 120 which is not coated with rhodopsin, Rho 532 nm off refers to a reflectance obtained when rhodopsin applied to the sensing element 120 is not irradiated with a light source with a wavelength of 532 nm, and Rho 532 nm on refers to a reflectance obtained after rhodopsin applied to the sensing element 120 is irradiated with a light source with a wavelength of 532 nm. That is, photoreactions are induced using the sensing elements 120 having a resonance frequency of 0.8, 1.0 or 1.7 THz, and then in comparison with the natural vibration modes of changed all-trans-retinal, a difference in signals before and after the photoelectric reaction is obtained.

Referring to graphs of FIGS. 8(*a*), (*b*) and (*c*) shown in green and black, it can be seen that there is no change in signals before and after the photoreaction at approximately 0.8 THz and 1.0 THz, that is, according to the absence or presence of light, and then the signal is changed at approximately 1.7 THz according to the absence or presence of light.

That is, it can be seen that rhodopsin having the natural vibration mode of approximately 1.7 THz shows a reaction according to the irradiation of light. According to the result shown in FIGS. 8a to 8c, the mode of approximately 1.5 to 1.9 THz among the natural vibration modes of all-trans-retinal shown by the photoreaction of rhodopsin is mainly observed, and therefore the sensing element 120 is designed to have strong resonance at approximately 1.5 to 1.9 THz in order to measure a degree of activation with respect to light of rhodopsin. Preferably, when rhodopsin is applied to the sensing element 120, a frequency is shifted by the refractive index of rhodopsin, and therefore the sensing element 120 may be formed to have the resonance frequency of 1.9 THz such that the frequency after the shift becomes 1.7 THz.

When the sensing element 120 is formed to cause resonance at a specific frequency according to the process described above, a reflectance of the sensing element 120 is first measured. That is, before the sensing element 120 is coated with rhodopsin, the electromagnetic wave irradiation unit 130 allows an electromagnetic wave to be incident in a direction perpendicular to the bottom surface of the sensing element 120, the detection unit 140 detects the electromagnetic wave reflected from the bottom surface of the sensing element 120, and the control unit 150 acquires a reflectance of the sensing element 120 itself. Afterward, when the sensing element 120 is coated with rhodopsin, the electromagnetic wave irradiation unit 130 allows an electromagnetic wave to be incident in a direction perpendicular to the bottom surface of the sensing element 120, the electromagnetic wave reflected from the bottom surface of the sensing element 120 is detected by the detection unit 140, and then the control unit 150 measures a first reflectance. Then, the light irradiation unit 110 allows rhodopsin applied to the sensing element 120 to be irradiated with light corresponding to a specific wavelength (e.g., 532 nm), the electromagnetic wave irradiation unit 130 allows an electromagnetic wave to be incident in a direction perpendicular to the bottom surface of the sensing element 120, the electromagnetic wave reflected from the bottom surface of the sensing element 120 is detected by the detection unit 140, and the control unit 150 measures a second reflectance. The results are shown in FIG. 9.

Figure 9:
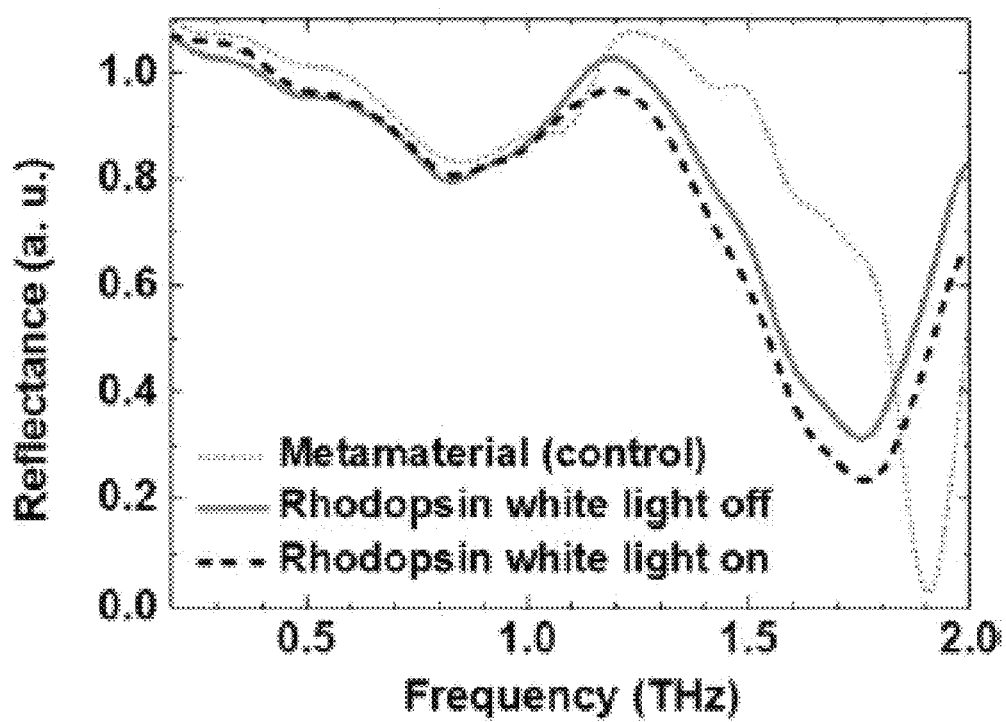
FIG. 9 is a graph showing photoreactivity of a protein according to white light.

FIG. 9 is a graph showing photoreactivity with respect to white light of a rhodopsin photoreceptor, and referring to FIG. 9, metamaterial (control) refers to a reflectance obtained while the sensing element 120 is not coated with rhodopsin, rhodopsin white light off refers to a reflectance obtained when the sensing element 120 is coated with rhodopsin, and light is not applied to the sensing element 120 (i.e., first reflectance), and rhodopsin white light on refers to a reflectance obtained when the sensing element 120 is coated with rhodopsin, and light is applied (i.e., second reflectance).

The control unit 150 quantifies a degree of photoelectric conversion in rhodopsin using the following Equation 1, based on the reflectance, the first reflectance and the second reflectance of the sensing element 120 itself.

$$\Delta R = \frac{R_{off} - R_{on}}{R_{ref}} \qquad \text{[Equation 1]}$$

Here, $R_{off}$ is a reflectance when the sensing element 120 is coated with rhodopsin, and there is no light irradiation (that is, first reflectance), $R_{on}$ is a reflectance when the sensing element 120 is coated with rhodopsin, and there is light irradiation (that is, second reflectance), and $R_{ref}$ is a reflectance while the sensing element 120 is not coated with rhodopsin.

Figure 10:
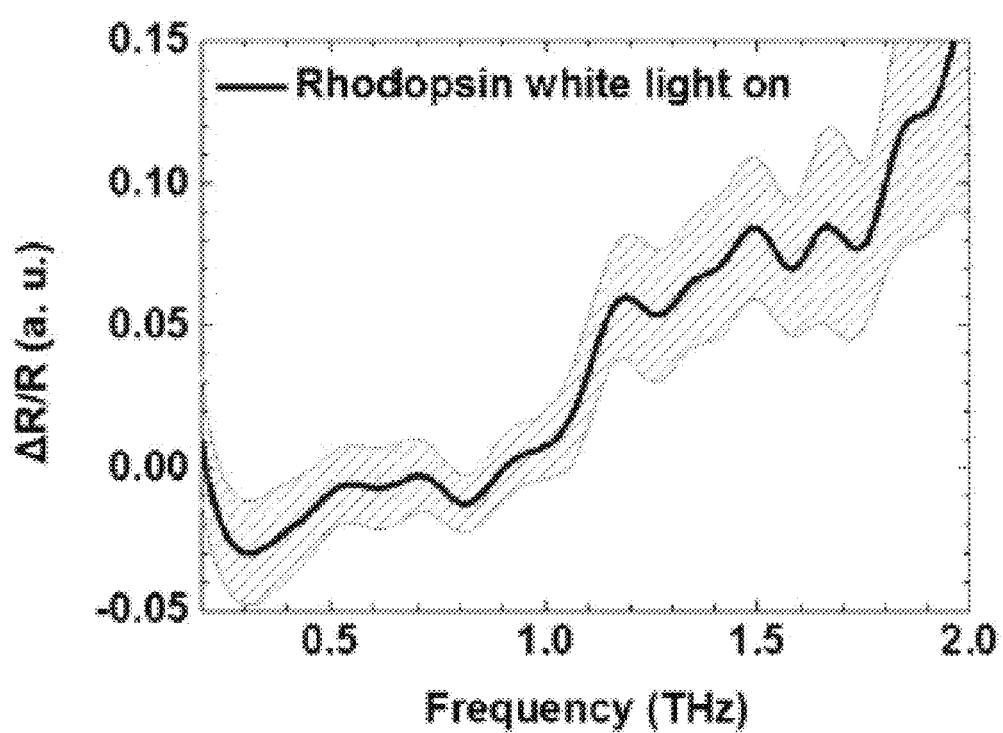
FIG. 10 is a graph showing an extracted photoreactive signal of a protein according to white light.

A rate of change in a signal calculated using Equation 1, based on the obtained reflectances shown in FIG. 9, is shown in FIG. 10. FIG. 10 shows a photoreactive signal with respect to white light of the rhodopsin photoreceptor extracted from the control unit 150, a region indicated by a solid line represents a tetrahertz signal absorbed by rhodopsin when rhodopsin is irradiated with light, and a region indicated by a dotted line represents a standard deviation. That is, when the conformation of the protein receptor is converted by an external light stimulus, the electromagnetic wave signal detected by the detection unit 140 is changed, and the control unit 150 may quantify a degree of photoelectric conversion actually occurring in the photoreceptor by estimating a rate of change in electromagnetic wave signals as shown in FIGS. 9 and 10.

When dynamic change such as conformational change occurs by exposing the photoreceptor protein to light, a change, for example, a part of the molecular chain is bent or twisted, resulting in the strong natural vibration mode of a specific frequency. When the photoreceptor protein absorbs a very low amount of an electromagnetic wave due to such a natural vibration mode, the amount of an electromagnetic wave reflected by the photoreceptor protein is changed. Accordingly, the system for observing the conformational change in a protein according to the present invention measures the reflectance of an electromagnetic wave changed according to the conformational change in the photoreceptor protein, thereby analyzing the dynamics such as the conformational change in the photoreceptor protein in real time.

Previously, a visual receptor GPCR which recognizes light in neurons to mediate a photoreaction has been described as an example, but the present invention is not limited thereto, and therefore a chain of reactions regulated by the conformational change in various receptors or membrane proteins, which are located on/in the cell membrane may be measured in real time. Particularly, the present invention relates to a measurement platform for quantitative data and dynamics on membrane-protein change corresponding to the earliest stage (upstream) in a signal transmission system. Conventionally, it is impossible to measure the activity of a receptor in real time, except with a receptor having the characteristics of an ion channel at the same time, in which the activity of the ion channel can be measured by an electro-physiological method. Therefore, to measure the activity of a receptor, living cells are cultured and then the intracellular change in the concentration of a secondary signal transmitter, caused by the change in activity of a G protein-coupled receptor is measured, or the change in the activity of a protein is traced, thereby indirectly measuring the activity of a receptor in the earliest stage. In addition, conventionally, to measure protein dynamics, a large amount of solid-phase sample is needed, and an experiment should be performed under an extreme condition, such as a low temperature.

However, by the system for observing the conformational change in a protein according to the present invention, a signal may be detected only with a very small amount of sample at atmospheric temperature, and since almost all cell responses to stimulation start from the conformational change in a cellular membrane protein, the use of the system for observing the conformational change in a protein according to the present invention may be expanded to the fields associated with the functional regulation in various cells in a human body, other than photoreceptors.

According to the present invention, as a change in a protein conformation accompanying activation is observed in real time by amplifying an electromagnetic wave signal of a specific frequency using a sensing element subjected to patterning of slots with a size of hundreds of nanometers (nm) and measuring a rate of the change in amplified signals, dynamics observed in a very small amount of protein sample can be observed in real time at room temperature, and thus sensitivity can be improved. As the reflectance of the electromagnetic wave is measured, the activity in a protein receptor can be naturally maintained.

In addition, a molecular sensing platform with high sensitivity and high selectivity is manufactured using terahertz electromagnetic wave-based photo-biosensor technology, and can be applied to measure various types of small biomolecules.

In addition, a metamaterial-based sensing element applied to the present invention can be subjected to tuning of resonance frequency in a wide frequency region by nanometer to micrometer scale conformations and various patterns, and an electromagnetic wave amplification phenomenon shown in the conformation of the sensing element is shown when an electromagnetic wave in the peripheral band of resonance frequency, inducing an increase in quantum mechanical absorption cross-section of a sample molecule. Therefore, compared to a conventional spectroscopic analysis method, the sensing element can be improved in sensitivity to a high level, and thus can be applied to detect a trace amount of sample and measure the change in dynamics in real time.

The preferred examples on the system for observing the conformational change in a protein according to the present invention have been described above, but the present invention is not limited thereto. It is possible to modify the examples in various ways within the scope of the claims, the detailed description of the present invention and the accompanying drawings, which also belong to the present invention.

EXPLANATION OF REFERENCE NUMERALS

100: system for observing the conformational change in a protein
110: light irradiation unit
111: light source
112: prism
113: color filter
120: sensing element
121: substrate
122: film
130: electromagnetic wave irradiation unit
140: detection unit
150: control unit

What is claimed is:
1. A system for observing a conformational change in a protein, comprising:
a sensing element including
a substrate having a plate shape, and
a film disposed on a top surface of the substrate and having slots configured to amplify an electromagnetic wave of a specific frequency;
a photoreceptor protein solution applied in the slots of the film;

a light irradiation unit which is configured to irradiate the photoreceptor protein solution with light from a top side of the substrate;

an electromagnetic wave irradiation unit separated from the light irradiation unit and configured to irradiate electromagnetic wave to the photoreceptor protein solution from a bottom side of the substrate such that the electromagnetic wave is incident in a direction perpendicular to a bottom surface of the sensing element;

a detection unit which is configured to detect the electromagnetic wave reflected from the photoreceptor protein solution; and a control unit which is configured to observe the conformational change in the photoreceptor protein based on the detected electromagnetic wave.

2. The system according to claim 1, wherein the slots have a rectangular shape.

3. The system according to claim 2, wherein the slots are regulated in width, thickness and length such that resonance occurs at a frequency in a natural vibration mode of the photoreceptor protein.

4. The system according to claim 1, wherein the light irradiation unit comprises a light source which emits the light, the light being white light;

a prism which separates the white light by wavelength; and a color filter which transmits only light with a specific wavelength out of light passing through the prism according to a wavelength dependence of the photoreceptor, wherein the light source, the prism and the color filter are arranged in order.

5. The system according to claim 1, wherein the electromagnetic wave irradiation unit irradiates the electromagnetic wave for a first reflection to the photoreceptor protein solution before the photoreceptor protein solution is irradiated with the light by the light irradiation unit, the detection unit detects the electromagnetic wave reflected from the photoreceptor protein solution, and the control unit measures the first reflectance based on the electromagnetic wave detected from the detection unit.

6. The system according to claim 5, wherein the electromagnetic wave irradiation unit irradiates the electromagnetic wave for a second reflection to the photoreceptor protein solution after the photoreceptor protein solution is irradiated with the light by the light irradiation unit, the detection unit which detects the electromagnetic wave reflected from the photoreceptor protein solution, and the control unit which measures the second reflectance based on the electromagnetic wave detected from the detection unit.

7. The system according to claim 6, wherein the control unit measures a rate of the change in a photoreactive signal of the photoreceptor protein based on the first reflectance and the second reflectance.

8. The system according to claim 1, wherein the photoreceptor protein solution applied in the slots of the film directly contacts with the top surface of the sensing element.

* * * * *